United States Patent [19]

Kotani et al.

[11] Patent Number: 4,935,368

[45] Date of Patent: Jun. 19, 1990

[54] PROCESS FOR PRODUCING TISSUE PLASMINOGEN ACTIVATOR

[75] Inventors: Ryotaro Kotani, Moriyama; Tsuneo Unuma, Ootsu; Shigeki Otawara, Ootsu; Setsuo Kobayashi, Ootsu; Tadao Suzuki, Urayasu, all of Japan

[73] Assignees: Toyo Boseki Kabushiki Kaisha, Osaka; Daiichi Seiyaku Co., Ltd., Tokyo, both of Japan

[21] Appl. No.: 879,779

[22] Filed: Jun. 27, 1986

[30] Foreign Application Priority Data

Jul. 1, 1985 [JP] Japan .................. 60-144368

[51] Int. Cl.$^5$ .................. C12N 9/64; C12N 9/50
[52] U.S. Cl. .................. 435/226; 435/212; 435/219; 435/240.2; 424/94.64
[58] Field of Search .............. 435/212, 215, 217, 226, 435/183, 240.2; 424/94.63, 94.64

[56] References Cited

U.S. PATENT DOCUMENTS 3,998,947 12/1976 D'Hinterland et al. ............. 424/105
4,568,544 2/1986 Hasegawa et al. ............. 435/215 X

FOREIGN PATENT DOCUMENTS 0099126 1/1984 European Pat. Off. .
0112122 6/1984 European Pat. Off. .
0143081 5/1985 European Pat. Off. .
0151996 8/1985 European Pat. Off. .

OTHER PUBLICATIONS

Rijken, D. et al., *J. Biolog. Chem.*, vol. 256, pp. 7035–7041, 1981.
Wallen, P. et al., *Biochimica et Biophysica Acta*, vol. 719, pp. 318–328, 1982.
Thorsen, S. et al., *Thromb Diathes Haemorrh* (Stuttg), vol. 32, pp. 306–324, 1974.
Thorsen, S. *Biochimica et Biophysica Acta*, vol. 393, pp. 55–65, 1975.
Denk, S. et al., New Aspects Trasylol Therapy, vol. 8, pp. 49–59, 1975.
Thorsen, S. et al., *Proc. Soc. Exp. Biol. Med.*, vol. 130(3), pp. 811–813, 1969.
Maki, M. et al., Chem. Abstracts, vol. 77, 43825e, p. 90, 1972.
Browne, M. et al., Gene, vol. 33, pp. 279–284, 1985.

*Primary Examiner*—Thomas G. Wiseman
*Assistant Examiner*—Charles L. Patterson, Jr.
*Attorney, Agent, or Firm*—Armstrong, Nikaido, Marmelstein, Kubovcik & Murray

[57] ABSTRACT

This invention discloses a process for producing tissue plasminogen activator. The process comprises cultivating *Escherichia coli*, yeast, or mammalian cells into which the vector having the gene for human tissue plasminogen activator (tPA) has been introduced by the recombinant DNA technology. In the cultivation or purification process, a specific antiplasmin agent, which is one of the protease inhibitors, is added to the medium and/or the buffer solutions used for purification, so as to prevent the conversion of single-chain form tPA into double-chain form tPA by a protease which is present in the medium.

5 Claims, No Drawings

PROCESS FOR PRODUCING TISSUE PLASMINOGEN ACTIVATOR

BACKGROUND OF THE INVENTION

1. Field of the Invention

The present invention relates to a process for producing a tissue plasminogen activator.

2. Description of the Prior Art

A tissue plasminogen activator (referred to as tPA hereinafter) has a strong affintiy for the thrombus and hence it readily brings about thrombolysis. Therefore, tPA can be used for the treatment of thrombosis.

At present, urokinase isolated from urine and streptokinase produced by certain strepococci are used as a thrombolytic agent base on plasminogen activation. However, they are poor in affinity for thrombi, and it is necessary to administer in a large dose to obtain the desirable effect. Moreover, they act not only on thrombi but also on fibrinogen and plasminogen in the blood. This leads to side effects such as internal hemorrhage. Under the circumstances, tPA is expected to be a new thrombolytic agent because of its strong affinity for the thrombus, and of thrombolysis in small doses with a minimum of side effect.

The tPA of human origin exists in an extremely small quantity in human normal tissues such as blood vessels, kidneys, and uteri. On the other hand, it can be isolated from the culture medium of a line of human melanoma cells and also from the culture medium of *Escherichia coli*, yeast, or mammalian cells into which the vector having the gene of human tPA has been introudced by the recombinant DNA technology. It is known that the tPA isolated from the culture medium can be divided into two classes according to the molecular structure. (Rijken, D. C. et al., J. Biol. Chem., Vol. 256 pp 7035-7041, 1981) The original tPA secreted by human melanoma cells has a single chain form composed of 527 amino acids and some sugar chains. In the culture medium, it is converted into tPA of 2-chain form by the action of a protease which exists in the culture medium. This protease cleaves the peptide bond between the 275th arginine and the 276th isoleucine counted from the amino terminus of the peptide chain, to give 2-chain form tPA, with the two strands being joined by one disulfide linkage. Therefore, the tPA isolated in the usual method from the culture medium is a mixture of single chain form tPA and 2-chain form tPA. It is recognized that these two kinds of tPA have a molecular weight of about 69,000 when measured by SDS-polyacrylamide gel electrophoresis under the non-reducing condition. However, under the reducing condition, it is recognized that single-chain form tPA has a molecular weight of about 69,000, and 2-chain form tPA has two values of molecular weight, 36,000 and 33,000.

It is an object of the present invention to provide a process for producing single-chain form tPA which is identical with the naturally occurring tPA. The thus produced tPA will be used as a medicine for medical treatment. This object, however, is not achieved by the conventional cultivation method, because the single-chain form tPA formed in the culture medium is readily converted into 2-chain form tPA by the action of proteases present in the culture medium. Therefore, it is necessary to add an inhibitor for these proteases into the culture medium prior to cultivation. The inhibitor should meet the following requirements. (a) It is effective in inhibiting proteases. (b) It can be easily removed from tPA when needed. (c) It is stable during purification of tPA. (d) It does not interfere with the process analysis and product analysis. (e) It is inexpensive enough to be used in an industrial scale production.

For the production of single-chain form tPA, Collen et al proposd that aprotinin ("Trasylol", a trade name of Bayer Co.), which is a protease inhibitor, should be added to the culture medium and to the buffer solution in the purification process. (Japanese Patent Kokai (Laid-open) No. 28009/82)

Aprotinin is a peptide having a molecular weight of 6500, extracted from bovine lungs and it is a foreign protein to human. Patients injected with aprotinin often suffer from shocks. (See "Yakumu Koho", No. 1271, P. 17, Aug. 11, 1984). Therefore, in case where tPA is used as an injection, it is necessary to remove aprotinin from tPA. completely. However, it is very difficult to remove aprotinin by the usual method without a loss of tPA. In addition, aprotinin is very expensive and it is uneconomical to use aprotinin for the commercial production of tPA. Another disadvantage of using aprotinin is that it interferes with the measurement of tPA activity by Fibrin Clot Lysis Time method (Rijken, D. C. et al., Biochim. Biophys. Acta, Vol. 193, pp 140-153, 1979) and in Fibrin Plate method (Jespersen, J. et al., Haemostasis, Vol. 13, pp 301-315, 1983). Moreover, aprotinin interferes with the determination of protein by Lowry method (Lowry, O. H. et al., J. Biol. Chem., Vol. 193, pp 265-275, 1951) by spectrophotometry at 280 nm.

the present inventors found that single-chain form tPA can be obtained by adding a specific antiplasmin agent, which is a protease inhibitor, to the culture media and all the buffer solutions in the purification process in order to prevent and/or inhibit the conversion of single-chain form tPA to 2-chain form tPA by proteases existing in the culture medium during cultivation process of human melanoma cells or *Escherichia coli*, yeast or mammalian cells which have been transformed by a vector carrying a gene encoding human tPA and during purification process. The present invention was completed on the basis of these findings.

SUMMARY OF THE INVENTION

Accordingly, it is an object of the present invention to provide a process for producing tPA, said process comprising cultivating tPA-producing cells in a medium containing an antiplasmin agent selected from the group consisting of ε-aminocaproic acid, trans-4-aminomethylcyclohexane carboxylic acid, trans-4-aminoethylcyclohexanecarboxylic acid, and esters thereof, and [ethyl-4-(6-guanidinohexanoyloxy)-benzoate]methansulfonate, and subsequently collecting tPA from the resulting cells or culture medium.

It is another object of the invention to provide a process for producing tPA, said process comprising cultivating tPA-producing cells in a medium and subsequently collecting tPA from the resulting cells or culure medium by using a buffer solution containing an antiplasmin agent selected from the group consisting of ε-aminocaproic acid, trans-4-aminomethylcyclohexane carboxylic acid, trans-4-aminoethylcyclohexane carboxylic acid, and esters thereof, and [ethyl-4-(6-guanidinohexanoyloxy)benzoate]methansulfonate.

DETAILED DESCRIPTION OF THE INVENTION

A ε-aminocaproic acid and esters thereof used in this invention include ε-aminocaproic acid, alkyl esters such as hexyl ε-aminocaproate, and aralkyl esters such as benzyl ε-aminocaproate.

Trans-4-aminomethylcyclohexanecarboxylic acid and esters thereof used in this invention include trans-4-aminomethylcyclohexanecarboxylic acid, aralkyl esters such as benzyl trans-aminomethylcyclohexanecarboxylate, and aryl ester such as phenyl trans-aminomethylcyclohexanecarboxylate and 4-(2-carboxyethyl)phenyl trans-aminomethylcyclohexanecarboxylate.

Trans-4-aminoethylcyclohexanecarboxylic acid and esters thereof used in this invention include trans-4-aminoethylcyclohexanecarboxylic acid, aralkyl esters such as benzyl trans-aminoethylcyclohexanecarboxylate, and aryl esters such as phenyl trans-aminoethylcyclohexanecarboxylate and 4-(2-carboxyethyl)phenyl trans-aminoethylcyclohexanecarboxylate.

The antiplasmin agent used in the invention can also be used in the form of the hydrochloride if it has a free amino group.

In this invention, it is possible to use [ethyl-4-(6-guanidinohexanoyloxy)benzoate]methansulfonate.

These antiplasmin agents can be produced easily and economically by the conventional method. Moreover, they can be completely removed from the reaction mixture, if necessary, by dialysis or gel filtration.

The amount of the antiplasmin agent used in this invention varies depending on the concentration of proteases existing in the culture medium. The amount to be added to the medium is 0.03 to 30 mg/ml, preferably 0.06 to 3 mg/ml. The amount to be added to the buffer solutions used in the purification process in 0.0001 to 30 mg/ml, preferably 0.0003 to 3 kmg/l. The effectiveness of preventing the conversion reaction is not satisfactory if the amount is less than 0.03 mg/ml in the cultivation process or less than 0.0001 mg/ml in the purification process. It is a waste of antiplasmin agent to use it in excess of 30 mg/ml in the cultivation and purification process in order to prevent the conversion reaction.

The antiplasmin agent should be added to the culture medium prior to the start of culture.

The antiplasmin agent used in this invention may be completely removed by conventional methods such as dialysis and gel filtration, when needed.

As the tPA producing cella used in this invention, are included human melanoma cells, *Escherichia coli*, yeasts, and mammalian cells into which the vector having the tPA gene has been introduced by the aid of the recombinant DNA technology.

The process for preparing the recombinant cells is described as follows with respect to mammalian cells.

Human melanoma cells or human uterine tissue are homogenized in the presence of a ribonuclease inhibitor such as guanidine thiocyanate and all of RNA are separated by centrifugation. Messenger RNA (mRNA) is separated from the RNA by means of oligo dT affinity column chromatography. The mRNA is subjected to size fractionation by means of sucrose density-gradient centrifugation. The fractions containing the tPA-specific mRNA is identified by Northern blot technique.

The RNA is recovered from the thus identified fraction continuing tPA-specific mRNA. The single-stranded cDNA complementary to the mRNA is produced by means of reverse transcriptase, and the double-stranded cDNA is synthesized from the single-stranded cDNA by means of DNA polymerase I.

The resulting double-stranded cDNA is treated with S1 nuclease, and tailed with oligo dC to the termini, whereby the oligo dC tailed cDNA is prepared. The thus obtained cDNA having the oligo dC tails is introduced into linear pBR 322 plasmid having the oligo dC tails. The resulting vector is used to transform *Escherichia coli* cells, whereby the cDNA library is constructed. The positive cDNA clones are isolated from the cDNA library by means of colony hybridization method. Plasmid DNA is prepared from the isolated clone, and the sequence of the DNA is determined.

The tPA cDNA which encodes the entire tPA is constructed from several cDNAs, of which the sequences have been determined, by cleaving them by proper restriction enzymes and joining of the proper fragments by DNA ligase. The thus constructed tPA cDNA is introduced into a proper expression vector by means of the combination of cleavage by proper restriction enzymes, modification of termini, and joining by DNA ligase.

The expression vector in this invention contains the following DNA sequences. They are, in addition to tPA cDNA, all or a part of bovine papilloma virus DNA sequence, a part of pBR 322 plasmid DNA sequence, and a DNA sequence necessary for the expression of tPA cDNA. In some cases, it contains a DNA sequence which is effective for selecting the transformants harboring the expression vector.

The thus obtained expression vector is transformed into proper host cells such as mouse cells.

The thus obtained transformed cells are cultured in the presence of antiplasmin agent of this invention in an amount of 0.03 to 30 mg/ml, whereby single-chain form tPA is produced.

As examples of the medium for culturing the recombinant cells, are included Eagle's minimum essential medium, Dulbecco's modified Eagle's medium, 199 medium, RPMI 1640 medium, Ham's F12 medium, and Iscov's modified Dulbecco's medium (GIBCO Laboratories). In the growth phase of cells, the medium is supplemented with 5 to 20 vol % (based on the medium) of fetal bovine serum or new born calf serum.

It is important to keep the culture temperature between 36° and 37° C. and pH of the medium between pH 6.5 and 7.5. The number of cells for inoculation is $5 \times 10^4$ to $1 \times 10^5$ per ml of medium, and the period of growth is 3 to 6 days. On the other hand, there is no limit relating to culture term for the production of tPA.

The single-chain form tPA produced as mentioned above can be easily purified by the conventional methods (as described by Rijken, D. C. et al., J. Biol. Chem., Vol. 256, pp 7035–7041, 1981) in the presence of the antiplasmin agent of the invention in an amount of 0.0001 to 30 mg/ml.

The buffer solution used in the purification process includes such as Tris buffer and, phosphate buffer. The buffer solution can be used in combination with detergents such as 0.01 to 0.1 w/v % of alkyl ether-based or polyethylene glycol-based nonionic detergents. The buffer solution can also be used together with a salt such as sodium chloride and potassium chloride.

Purification may be accomplished by conventional ion exchange chromatography and by affinity chromatography which employs a resin having a dye, a lectin, a hydrophobic group, and amino acid, a substrate analog, a metal chelate, etc.; or by gel filtration. Highly pure tPA can be recovered by the combination of the above two or three methods at a high yield.

According to this invention, a specific antiplasmin agent is used in the culture process or purification process. Use of very small amount of antiplasmin agent can prevent the conversion reaction from single-chain form tPA into 2-chain form tPA.

The tPA obtained according to the process of this invention was analyzed by SDS-polyacrylamide gel electrophoresis under the reducing condition. (Weber, K. et al., J. Biol. Chem., Vol. 244, pp 4406–4412, 1969) The results indicated that there were no 2-chain form tPA present.

The invention is now illustrated by the following examples.

EXAMPLE 1

Human melanoma cells were grown at 37° C. for 5 days in a Dulbecco's modified Eagle's medium (GIBCO Laboratories) supplemented with sodium bicarbonate (final concentration, 0.19%), L-glutamine (final concentration, 0.06%), and fetal bovine serum (final concentration, 10%). The cells grown were separated from the medium and washed thoroughly with Dulbecco's phosphate buffer solution (Flow Laboratories).

The culture of the cells was continued at 37° C. for 3 days using the above-mentioned proliferation medium containing no fetal bovine serum, in the presence or absence of the antiplasmin agent (A) of this invention. The medium was collected and centrifuged at 7500×g at 4° C. for 15 minutes. The resulting supernatant fluid was preserved at −20° C. until use. The amount of protein in the supernatant fluid determined by Lowry method after dialysis was about 150 mg/liter, and the tPA activity measured by the Fibrin Clot Lysis Time method (referred to as FCLT method hereinafter) was 50 IU/ml. The activity was measured in comparison with the standard urokinase provided by Japanese Ministry of Welfare.

The purification of the tPA obtained from the culture medium was accomplished according to the above-mentioned Rijken's method, in the presence or absence of the antiplasmin agent (A) of this invention. In other words, the culture medium was treated with zinc chelate Sepharose (made by Pharmacia), and then with concanovalin A Sepharose (made by Pharmacia), and finally subjected to gel filtration using Sephadex G-150 (made by Pharmacia).

After treatment with Sephadex G-150, the protein concentration in the solution was 33 µg/ml and the tPA activity was 2700 IU/ml. The treated solution was analyed by SDS-polyacrylamide gel electrophoresis according to the above-mentioned Weber's method. The gel concentration was 10%. The apparatus was of slab type (made by Marysol Industry Co., Ltd.) Electrophoresis was carried out at room temperature for 4 hours with a constant current of 10 mA. After electrophoresis, the protein was stained with Coomassie Brilliant Blue R250 (0.25%) and then destained with a mixture of 10% acetic acid and 10% methanol. The ratio of single-chain form tPA and 2-chain form tPA was determined by using an ultrascan laser densitometer (LKB Co.).

Table 1 shows the result of SDS-polyacrylamide gel electrophoresis of the tPA derived from human melanoma cells.

For comparison, the same procedure as mentioned above was repeated to produce tPA, except that antiplasmin agent A was replaced by either antiplasmin agent B or aprotinin. The results are shown in Table 1.

TABLE 1

| | Antiplasmin agent | Amount of antiplasmin agent in medium *1 | in buffer *1 | Single chain form tPA (%) |
|---|---|---|---|---|
| Example 1 | A *2 | 0.034 mg/ml | 0.034 mg/ml | 95 |
| | | 0.34 | 0.34 | 100 |
| | | 3.4 | 3.4 | 100 |
| | | 3.4 | — | 65 |
| | | — | 3.4 | 55 |
| | | — | — | 21 |
| | B *3 | 2.7 | 2.7 | 98 |
| Comparative Example | Aprotinin | 6.5 | 6.5 | 97 |

*1 The medium and the buffer for purification were sterilized by filtration through a 0.22µ filter before use.
*2 4-(2-carboxyethyl)phenyl trans-4-aminomethyl-cyclohexanecarboxylate
*3 Phenyl trans-4-aminoethylcyclohexanecarboxylate It is noted from Table 1 that the antiplasmin agent is by far superior to aprotinin in the productivity of single-chain form tPA. It is also noted that the addition of antiplasmin agent either to the medium alone or the buffer alone yielded more single-chain form tPA than the addition of no antiplasmin agent to either of them. Single-chain form tPA was produced at a high yield when the antiplasmin agent was added to both the medium and the buffers.

EXAMPLE 2

The same procedure as in Example 1 was repeated except that the human melanoma cells were replaced by the mouse cells into which the vector having the human tPA gene had been introduced by the recombinant DNA technology. The cells are C127 mouse cells transformed with plasmid pCAT, containing the gene encoding human uterine t-PA, as described in U.S. patent application Ser. No. 656,770 filed October 1, 1984, herein incorporated by reference. Construction of the plasmid is also described in European Patent Publication No. A2 0 178 105. The transformed cells were obtained from Integrated Genetics, Inc., Framingham Mass. Table 2 shows the result of with SDS-polyacrylamide gel electrophoresis of the tPA derived from the cells having recombinant DNA.

TABLE 2

| | Antiplasmin agent | Amount of antiplasmin agent in medium *1 | in buffer *1 | Single chain form tPA (%) |
|---|---|---|---|---|
| Example 2 | A *2 | 0.034 mg/ml | 0.034 mg/ml | 96 |
| | | 0.34 | 0.34 | 100 |
| | | 0 | 0 | 15 |
| | E *3 | 0.36 | 0.36 | 98 |
| | | 3.6 | 3.6 | 100 |
| Comparative Example | Aprotinin | 6.5 | 6.5 | 98 |

*1 The medium and the buffer for purification were sterilized by filtration through a 0.22µ filter before use.
*2 4-(2-carboxyethyl)phenyl trans-4-aminomethyl-cyclohexanecarboxylate
*3 4-(2-carboxyethyl)phenyl trans-4-aminoethyl-cyclohexanecarboxylate

EXAMPLE 3

The same procedure as Example 1 was repeated except that the medium was sterilized by heating at 121°

C. for 20 minutes instead of filtration. The results are shown in Table 3.

TABLE 3

| | Antiplasmin agent | Amount of antiplasmin agent in medium | Amount of antiplasmin agent in buffer | Single-chain form tPA (%) |
|---|---|---|---|---|
| Example 3 | A *1 | 0.34 mg/ml | 0.34 mg/ml | 97 |
| | | 3.4 | 3.4 | 99 |
| | C *2 | 1.3 | 1.3 | 95 |
| Comparative Example | Aprotinin | 6.5 | 6.5 | 53 |

*1 4-(2-carboxyethyl)phenyl trans-4-aminomethyl-cyclohexanecarboxylate
*2 ε-Aminocaproic acid For industrial cultivation, the medium is usually sterilized by heating, and aprotinin is inactivated under such conditions. However, it is noted that the antiplasmin agent of this invention was stable and retained its effectiveness after heat sterilization.

What is claimed is:

1. A process for producing human tissue plasminogen activator, said process comprising cultivating cells capable of producng tissue plasminogen activator in a medium containing an inhibitorily effective amount of an antiplasmin agent selected from the group consisting of trans-4-aminomethylcyclohexane carboxylic acid, and esters and salts thereof, under culture conditions sufficient to produce tissue; plasminogen activator and subsequently collecting tissue plasminogen activator from the resulting cells or culture medium.

2. A process for producing human tissue plasminogen activator, said process comprising cultivating cells capable of producing tissue plasminogen activator in a medium under culture conditions sufficient to produce tissue plasminogen activator and subsequently collecting tissue plasminogen activator from the resulting cells or culture medium by using a buffer solution containing an inhibitorily effective amount of an antiplasmin agent selected from the group consisting of trans-4-aminomethylcyclohexane carboxylic acid and esters and salts thereof.

3. A process according to claim 1, wherein the cells are mouse cells.

4. A process according to claim 2, wherein the cells are mouse cells.

5. A process for producing human tissue plasminogen activator, said process comprising cultivating cells capable of producing tissue plasminogen activator in a medium containing an inhibitorily effective amount of an antiplasmin agent selected from the group consisting of trans-4-aminomethylcyclohexane carboxylic acid, and esters and salts thereof, under culture conditions sufficient to produce tissue plasminogen activator, and subsequently collecting tissue plasminogen activator from the resulting cells or culture medium by using a buffer solution containing an inhibitorily effective amount of an antiplasmin agent selected from the group consisisting of trans-4-aminomethylcyclohexane carboxylic acid and esters and salts thereof.

* * * * *